United States Patent [19]

Manne

[11] 4,015,332
[45] Apr. 5, 1977

[54] CROWN FORM AND METHOD

[76] Inventor: John E. Manne, 64 Delmar Place, Delmar, N.Y. 12054

[22] Filed: Sept. 23, 1975

[21] Appl. No.: 615,914

[52] U.S. Cl. .................................................. 32/12
[51] Int. Cl.² ......................................... A61C 5/08
[58] Field of Search ................................... 32/12, 8

[56] References Cited

UNITED STATES PATENTS

| | | | |
|---|---|---|---|
| 515,400 | 2/1894 | Harrell | 32/12 |
| 2,558,139 | 6/1957 | Knock | 32/12 X |
| 3,120,704 | 2/1964 | Newcomb | 32/12 |
| 3,140,543 | 7/1964 | Menter | 32/12 |
| 3,585,723 | 6/1971 | Simor | 32/12 |

OTHER PUBLICATIONS

"Rentive Cups for Acrylic Jacket Crowns", *Dental Digest*, Oct., 1944, p. 467.

Primary Examiner—Robert Peshock
Attorney, Agent, or Firm—Kane, Dalsimer, Kane, Sullivan and Kurucz

[57] ABSTRACT

The disclosure is of a novel dental crown form and the method of its installation. The crown form of the invention is a tubular shell of a flexible polymeric resin corresponding generally to the configuration of a natural tooth. An embodiment of the crown form may be characterized in part by the means for fluid communication between the interior and the exterior of the shell, in the sidewall at points on the surface corresponding to the mesial and distal tooth surfaces. When applied to a tooth stump, filler is forced from the shell interior through the means to establish contact with adjacent teeth. The cured filler so expressed supports the crown form in position. The crown forms of the invention are also characterized by slits in specific positions of the shell sidewalls, having a uniform width. The slits permit the crown forms to flex open and closed along a hinge axis on the occlusal surface, thereby facilitating installation on a variety of tooth sizes. The method of the invention comprises, briefly, installing the form of the invention on a prepared natural tooth so the filler used is expressed through the aforementioned means to cure and anchor the form to adjacent teeth.

12 Claims, 4 Drawing Figures

CROWN FORM AND METHOD

BACKGROUND OF THE INVENTION

1. Field of the Invention

The invention relates to dental crown forms and the method of installing dental crown forms.

2. Brief Description of the Prior Art

The installation of permanent crowns to reconstruct a tooth, particularly human teeth, is a commonplace procedure generally accomplished in a sequence of steps over a prolonged period of time. Initially, impressions of the tooth to be reconstructed may be made to establish relationships with adjacent teeth. Then the tooth is ground to remove damaged portions and to provide a shape or "stump" which is adapted to receive the crown jacket. Impressions or a mold is made of the shaped stump for transmittal to a dental laboratory where the permanent crown is molded. Prior to permanent fixation of the crown, a number of fittings may be required. In the meantime, it is necessary to protect the shaped tooth or stump from shock, further damage and exposure which could ultimately result in loss of the tooth. To accomplish this, a temporary crown or "crown form" is installed on the shaped tooth immediately. Desirably, the crown form is quickly installed, well fitting, durable, easily removed and replaced and completely protective of the shaped tooth.

Conventional crown forms come in several types. One type is a shell of thin metal such as aluminum or copper. They are affixed by lining with a fluid dental cement and forcing over the shaped tooth. As supplied, these metal crown forms generally do not correspond closely to the configuration of the tooth to be protected. For proper installation the shape of the form must be altered by the operator in an effort to fit the tooth. For example, if the crown form is too long, it must be trimmed along the cervical edge and festooned to correspond to the gum line. In addition, the open end of the metal crown form may have to be crimped inwardly to reduce its lateral dimension and to provide a configuration similar to that of the cervical end of a tooth. Such contouring is difficult to carry out without causing folds in the material of the crown form. In any event, the material of the crown never can be gathered in sufficiently to produce a close fit with the tooth. As a result, there is a projecting edge at the cervix of the crown form that is irritating to the gum tissue and uncomfortable to the patient.

Another difficulty of the metallic crown form resides in carrying out its installation. An excessive amount of dental cement is used to line the crown form and then it is forced over the shaped tooth. This expresses the excess cement through the cervical opening, under pressure. If the cement sets, additional steps are required to cut or grind away the excess cement adhering to the cervical line of the crown form. To overcome this, it has been suggested to place vent holes in the lingual or occlusal surfaces of the crown form. However, the cement expressed through vent holes positioned in those locations, upon setting, must also be removed as it is discomforting to the patient.

The metallic crown forms suffer other disadvantages, re; oxidation in oral fluids and their lack of color appeal. To meet these objections, celluloid crown forms were introduced. Although these forms presented a number of advantages over the metal crowns, they require cutting to obtain a good fit and are difficult to remove when removal is desired. These characteristics make use of the celluloid forms time consuming for the busy operator. The celluloid crown form also poses the same problem of expressing excess cement along the cervical edge, requiring removal, as described above in relation to the metal forms.

In recent years, synthetic polymeric resin (polycarbonate) forms have become commercially available. These forms are durable, but large inventories of shapes and sizes must be maintained since they are difficult to adapt to any given shape or size. Unless one is fortunate enough to find a form which is a perfect mate to the shaped tooth, extensive cutting is required to adapt the form. Much of the cutting requires grinding with a grindstone, which causes a "balling" of the plastic. Further, the commercially available polycarbonate crown forms suffer from the disadvantages of the prior crown forms, ie; the cervical edges must be trimmed, festooned and later trimmed of excess cement expressed through the cervical opening during insertion over the shaped tooth. Further, the commercially available polycarbonate crown forms generally fail to make mesial-distal tooth contact properly because they are not adjustable in this direction without extensive modification.

The crown forms of my invention are an improvement over the prior art crown forms in a number of respects. For example, they include a hinge structure so that they will accommodate teeth of variable dimensions. This is particularly valuable when fitting the crown to molar teeth and reduces the time required for preparing the crown form. Further, the new crown form of my invention may be cut with scissors when necessary to trim the cervical line. This eliminates the "balling" of the plastic caused by application of a grindstone. The unique positioning of a means for allowing the escape of excess dental cement from the interior of the crown form during installation facilitates the serial assembly, as in replacement of missing teeth, in a fixed prosthesis and serves to anchor single units. This is a particular advantage when installing a single crown form since most of the dental cements employed require at least 48 hours before full strength is achieved. During this setting period, initial mastication can drive the crown form further onto the shaped tooth. If the occlusal surface falls beneath the level of the adjacent teeth, a hypo-occlusion occurs. Therefore, no pressure is received by the temporarily crowned tooth during occlusion. The tooth may then erupt from its original position or the opposing tooth will drift toward the crown tooth. Later when the permanent crown is applied, it will not occupy the same position relative to the opposing tooth that it was originally made for, causing a hyper-occlusion. This problem is less likely to occur when the single crown form, as installed initially, is anchored or bridged to the adjacent teeth.

The novel crown forms of the invention provide the means for the method of the invention. The method of the invention as described hereafter, has advantages of speed, economy of materials and results in a better fitting, more comfortable prosthesis.

SUMMARY OF THE INVENTION

The invention comprises a dental crown form, which comprises; a tubular shell corresponding generally in configuration and dimension to a natural tooth, fabricated from a flexible synthetic, polymeric resin and having (i) a closed first end, the exterior thereof defining an occlusal surface corresponding in configuration and dimension to the occlusal surface of a natural tooth; (ii) a restricted, open second end which is festooned in a contour to correspond generally to the cervical line of a natural tooth; (iii) sidewalls flaring outwardly from said open second end, and integral with said closed first end, said sidewalls corresponding in configuration and dimension to the mesial, distal, lingual and buccal surfaces, respectively, of a natural tooth; and (iiii) means for fluid communication between the interior and the exterior of said shell, in the sidewall at points on the surfaces corresponding to said mesial and said distal surfaces; said sidewalls having a plurality of slits therein, at least two of which are positioned in surfaces opposite to each other, said slits being substantially uniform in width throughout their length and originating at the open second end and terminating at a point in the sidewall; provided that when said shell corresponds to the configuration and dimension of a tooth selected from the group consisting of a pre-molar, a canine and an incisor, said surfaces opposite to each other are the mesial and distal surfaces and when said shell corresponds in configuration and dimension to a molar tooth, said surfaces opposite to each other are the lingual and buccal surfaces, respectively.

The invention also comprises a method of protecting a natural tooth with a dental crown form, which comprises; (a) shaping said tooth to receive a dental crown form; (b) providing a dental crown form of the invention as described above; (c) applying a dental cement filler to the inside surfaces of said shell; (d) forcing said crown form onto the shaped tooth so that a portion of said filler is expressed through said means for fluid communication, to the exterior of said shell and into contact with adjacent teeth; (e) allowing said dental cement filler to set, whereby said crown form is held engaged to said shaped tooth and is anchored to the adjacent teeth.

DETAILED DISCLOSURE OF THE PREFERRED EMBODIMENTS OF THE INVENTION

Figure 1:
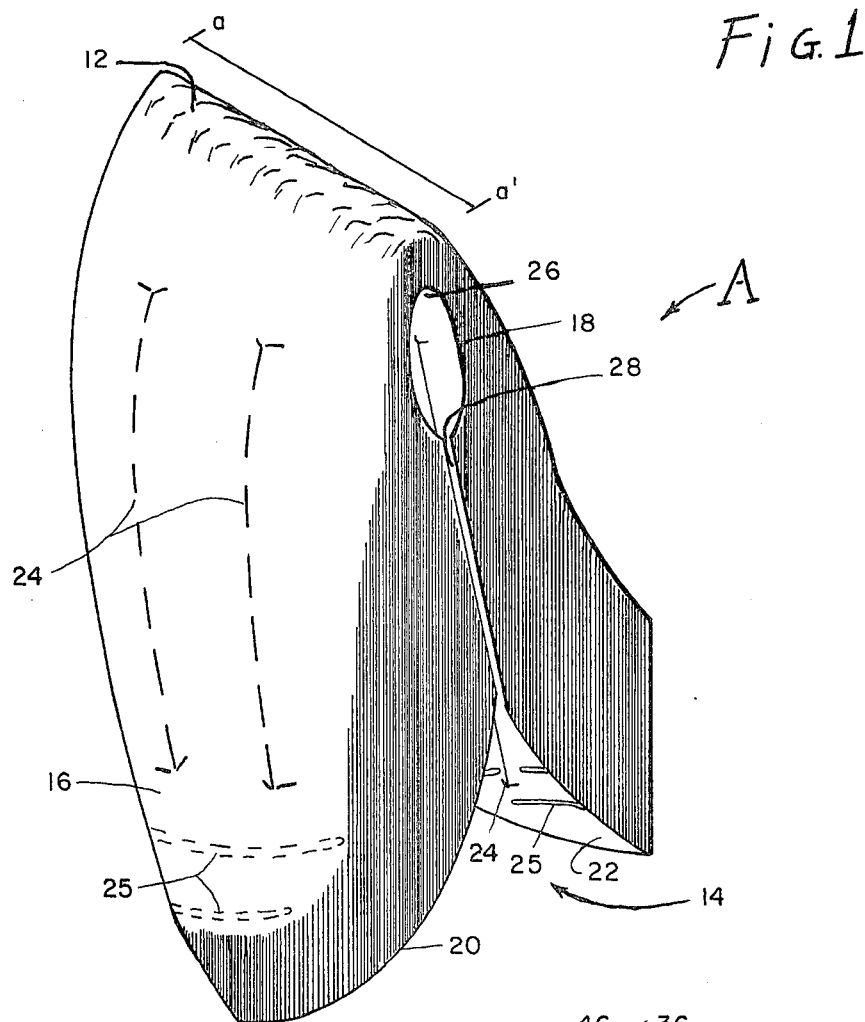
FIG. 1 is an isometric view of a preferred embodiment crown form of the invention showing surfaces corresponding to the buccal and mesial or distal surfaces of a natural incisor tooth.

An understanding of the invention may be obtained by referring to the accompanying drawings of FIGS. 1-4, inclusive. FIG. 1 is an isometric view of a preferred embodiment crown form A of the invention intended to have the configuration and dimension of a natural human incisor. In conforming to a natural human incisor, the form A presents a tubular shell-like appearance with one closed end corresponding to the incisol edge 12 and sidewalls which generally flare outward from the open opposite end 14 to edge 12 to present a buccal surface 16, a mesial (or distal) surface 18 and a lingual surface (not seen in FIG. 1.). The open end 14 is festooned to mimic the cervical line 20 of a natural tooth. The tubular form A is hollow, the inner surfaces 22 defining a space for receiving the prepared stump of a natural tooth to be crowned as will hereinafter be described in greater detail. In the preferred embodiment of FIG. 1, the inner surface 22 has ridges 24 parallel to the long axis of the sidewall as a means for retaining an applied fluid dental cement as will also be described hereinafter in greater detail. There can also be horizontal grooves 25 in the cervical region for the same purpose.

The crown form A may be fabricated from any synthetic polymeric resin having a degree of flexibility and which is conventionally employed in fabricating dental prosthetics. A preferred resin for the fabrication of the crown form A is a polycarbonate resin. The methods and apparatus for fabricating polycarbonate resin shells is generally well known to those skilled in the art and need not be recited in detail herein.

Essential to the structure of the form A is a means for fluid communication between the interior and the exterior of form A on the surfaces corresponding to the mesial and distal surfaces 18 of a natural tooth. In the embodiment form A the means employed is an aperture 26 through surface 18. The dimensions of aperture 26 must be large enough to allow a thick enough connection between crown forms in a bridge to prevent breaking during mastication. Illustratively 1 to 3 mm. is generally sufficient, preferably circa 5 mm on back forms. As shown in the FIG. 1, the aperture is preferably elliptical in shape with the long axis of the ellipse vertical.

A further necessary structure in the crown forms of the invention are splits 28 in the sidewalls, which originate at the cervical line 20 and terminate at a point in the sidewall short of the edge 12. The splits 28 in the sidewall are preferably of a uniform width throughout their length and when the means for fluid communication is an aperture 26, the splits 28 preferably terminate in said apertures 26. The splits 28 are positioned in the sidewalls at positions opposite each other. More specifically, when the dental crown form corresponds in configuration to a premolar, a canine or an incisor as shown in form A, the splits 28 are in the sidewalls corresponding to the mesial 18 and distal surfaces (not seen in FIG. 1.).

The combination of flexibility in the polymer resin from which form A is fabricated plus the splits 28 provide a structure having a hinge-like action along the axis $a-a'$. This hinge action permits the form A to expand when form A is forced over the stump of a tooth to be crowned, said stump having a larger diameter than the restricted opening in end 14 of the crown form A. The natural resiliency of the structure, after expansion, forces the buccal surface 16 and the lingual surface against the tooth stump, whereby frictional engagement holds the form A in position on the tooth stump. The expandable form A can be used to fit a variety of tooth dimensions, but several different widths may be manufactured to simplify fitting.

Figure 2:
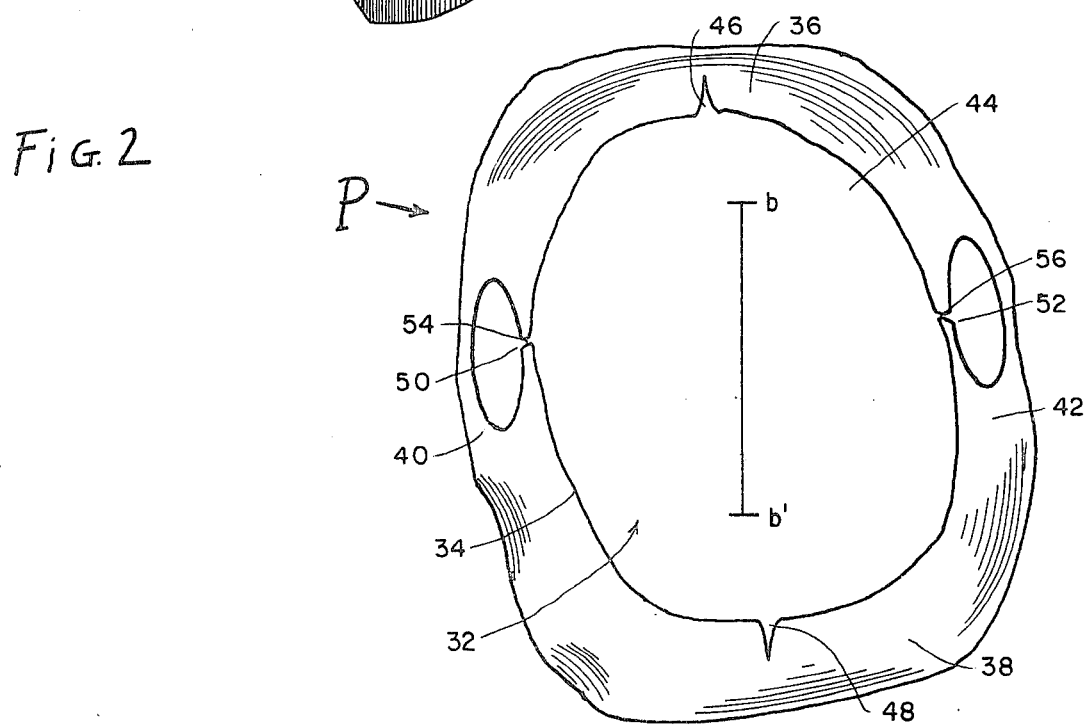
FIG. 2 is a view-in-perspective from the open end of a preferred embodiment crown form of the invention corresponding to the configuration and dimension of a natural molar tooth.

Referring now to FIG. 2, a view-in-perspective from the open end of a preferred embodiment crown form P of the invention corresponding to the configuration and dimension of a natural molar tooth, there is seen the open end 32 defined by cervical line 34 which forms the lower edge of sidewalls comprising a lingual surface 36, a buccal surface 38, a mesial surface 40 and a distal surface 42, all of which converge into an occlusal surface seen from its inner side 44. As shown in FIG, 2, the sidewalls generally flare outward from the cervical line 34 to the occlusal surface so that the open end 32 is a restricted opening into the space defined by the crown form P. In lingual surface 36 and buccal surface 38 are slits 46 and 48 originating at the cervical line 34 and terminating at points in the sidewalls short of the occlusal surface. These slits 46 and 48, positioned in opposition to each other, in combination with the natural flexibility of the resin from which form P is fabricated, provides a hinge-like action of the form P along the axis $b-b'$, of the form P. This permits mesial surface 40 and distal surface 42 to be flexed away from one another, thereby expanding the restricted opening 32 when it is desired to mount the form P on the stump of a tooth having a diameter slightly larger than the diameter of restricted opening 32. Upon release of the flexed surfaces 40 and 42 their tendency to return to a normally unflexed position brings these sidewalls into frictional engagement with the then covered tooth stump, thereby holding the crown form P in an initial position. Apertures 50 and 52 are shown in the mesial 40 and distal surfaces 42 respectively as a means for fluid communication between the inside and outside of form P. As shown, the apertures 50 and 52 are preferably elliptical in shape, having the long axis running horizontally to the tooth. The apertures 50 and 52 may also be round in configuration. Slits 54 and 56 are necessary and originate at the cervical line 34, traverse the mesial 40 and distal 42 surfaces, respectively, terminating in apertures 50 and 52, respectively. These slits 54 and 56 provide for further expansion of the restricted opening 32 as described above when fitting the form P over the prepared and shaped stump of a molar tooth to be crowned.

Figure 3:
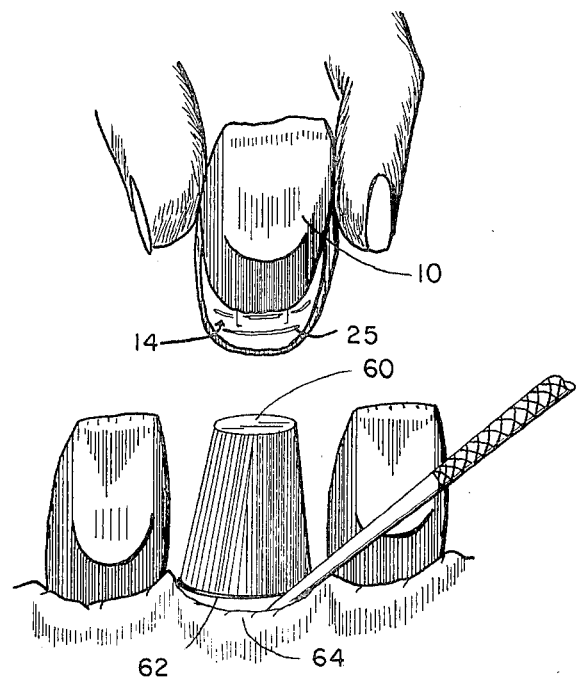
FIG. 3 is an isometric view of the embodiment of FIG. 1 being fitted on the shaped and prepared stum of an incisor tooth.
Figure 4:
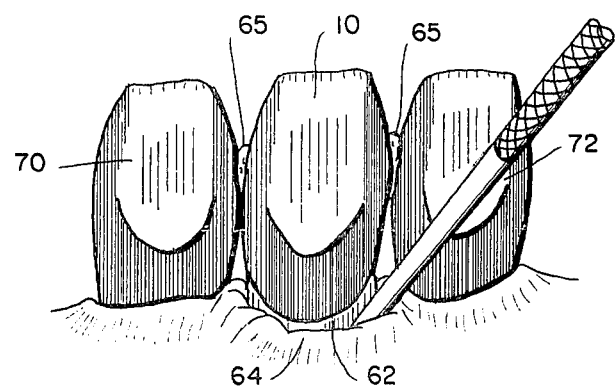
FIG. 4 is an isometric view as seen in FIG. 3 but after affixation of the crown form to the prepared incisor tooth.

The method of the invention may be followed by referring now also to FIGS, 3 and 4. In FIG. 3, there is shown a prepared and shaped incisor tooth 60, prepared to receive a crown in the conventional way by grinding away enamel, leaving some enamel 62 under the gum line 64. A crown form A, conforming in configuration and dimension to a natural incisor tooth is made ready by coating the inner surfaces 22 with an excess of a conventional dental cement filler. In the preferred embodiment form A, the ridges 24 parallel to the long axis of the inner sidewall surfaces 22 serve to assist in retaining the dental cement filler in place while the crown form A is inserted over the shaped tooth 60. During insertion, the opening 14 expands as the form A flexes along the $a-a'$ axis, with the lingual and buccal surfaces moving apart along the borders formed by the slits 28,29 in the mesial and distal surfaces. The form A is pressed firmly onto shaped tooth 60 and the tendency of lingual surface and buccal surface 16 to spring back to close the expanded open end 14 holds the form A in place until the cement sets. The configuration of the slits being such that they have a uniform width substantially throughout their length is advantageous in assisting to have the lingual and buccal surfaces spring together to hold form A on tooth 60. If the slits were, for example wedge shaped, the tendency would be for the surfaces to spring apart unless held. Excess cement within form A is expressed through the apertures 26, 27 with trapped air so that a uniform and complete filling of voids between the inner surface 22 and tooth 60 occurs. The form A is thusly anchored to the shaped tooth 60 and upon setting of the cement is firmly positioned. As shown in FIG. 4, excess cement 65 expressed through apertures 26, 27 contact adjacent teeth 70 and 72 for support thereto and thereby further anchor the form A in place. When desired, the temporary crown A may be readily removed by pulling with Baade pliers. The form can then be repositioned on tooth 60 again without difficulty. The dental cement will also be expressed through slits in the sidewalls if they are not able to fully close because of the tooth 60 dimension. The expressed dental cement seals any such opening to protect the tooth stump 60.

Once inserted, the "bite" can be adjusted by adding fluid resin to occlusal surfaces and contouring the crown form.

Those skilled in the art will readily appreciate that the novel crown forms of the invention may be fitted to the shaped tooth more conveniently than the prior art crown forms. Accordingly, it is possible to install the crown forms of the invention very rapidly and with a minimum of time required for setting of the dental filler. Accordingly, in a preferred method of the invention, a dental cement filler is employed which will set in about 15 seconds. Preferred are the acrylic polymer resin dental cements which may be formulated to cure very rapidly by the cross-linking of acrylic polymers with acrylic monomer cross-linking agents. The method of the invention is also advantageously carried out with a minimum of laboratory preparation time as those skilled in the art will appreciate.

What is claimed:

1. A dental crown form, which comprises;

a tubular shell corresponding generally in configuration and dimension to a natural tooth, fabricated from a flexible, synthetic, polymeric resin and having i. a closed first end, the exterior thereof defining an occlusal surface corresponding in configuration and dimension to the occlusal surface of a natural tooth;

ii. a restricted, open second end which is festooned in a contour to correspond generally to the cervical line of a natural tooth;

iii. sidewalls flaring outwardly from said open second end and integral with said closed first end, said sidewalls corresponding in configuration and dimension to the mesial, distal, lingual and buccal surfaces, respectively, of a natural tooth; and iv. means for fluid communication between the interior and the exterior of said shell, in the sidewall at points on the surfaces corresponding to said mesial and said distal surfaces; said sidewall having a plurality of slits therein, at least two of which are positioned in surfaces opposite to each other, said slits being substantially uniform in width throughout their length and originating at the open second end and terminating at a point in the sidewall;

provided that when said shell corresponds to the configuration and dimension of a tooth selected from the group consisting of a pre-molar, a canine and an incisor, said surfaces opposite each other are the mesial and distal surfaces and when said shell corresponds in configuration and dimension to a molar tooth, said surfaces opposite to each other are the lingual and buccal surfaces, respectively.

2. A crown form according to claim 2 wherein the inner surface of said shell has a means on the sidewall thereof for retaining fluid dental cement.

3. A form according to claim 1 wherein said resin is a polycarbonate.

4. A form according to claim 1 wherein said means is an aperture in said sidewall.

5. A dental crown form, which comprises;
a tubular shell corresponding generally in configuration and dimension to a natural tooth, fabricated from a flexible, synthetic, polymeric resin and having
   i. a closed first end, the exterior thereof defining an occlusal surface corresponding in configuration and dimension to the occlusal, surface of a natural tooth;
   ii. a restricted, open second end which is festooned in a contour to correspond generally to the cervical line of a natural tooth;
   iii. sidewalls flaring outwardly from said open second end and integral with said closed first end, said sidewalls corresponding in configuration and dimension to the mesial, distal, lingual and buccal surfaces, respectively, of a natural tooth; and
   iv. apertures for fluid communication between the interior and the exterior of said shell, in the sidewalls at points on the surfaces corresponding to said mesial and said distal surfaces; said sidewall having a plurality of slits therein, at least one of which is positioned in a mesial and one of which is positioned in a distal surface, said slits being substantially uniform in width throughout their length and originating at the open second end and terminating at the aperture through the surface wherein said slit is positioned.

6. A form according to claim 5 wherein said tooth is selected from the group consisting of an incisor, a pre-molar and a canine.

7. A form according to claim 5 wherein said tooth is a molar.

8. A form according to claim 7 wherein there are additional slits opposite each other in the lingual and buccal surfaces, respectively.

9. A method of protecting a natural tooth with a dental crown form, which comprises;
   a. shaping said tooth to receive a dental crown form;
   b. providing a dental crown form which comprises a tubular shell corresponding generally in configuration and dimension to a natural tooth, fabricated from a flexible, synthetic, polymeric resin and having
      i. a closed first end, the exterior thereof defining an occlusal surface corresponding in configuration and dimension to the occlusal surface of a natural tooth;
      ii. a restricted, open second end which is festooned in a contour to correspond generally to the cervical line of a natural tooth;
      iii. sidewalls flaring outwardly from said open second end and integral with said closed first end, said sidewalls corresponding in configuration and dimension to the mesial, distal, lingual and buccal surfaces, respectively, of a natural tooth; and
      iv. means for fluid communication between the interior and the exterior of said shell, in the sidewall at points on the surfaces corresponding to said mesial and said distal surfaces; said sidewall having a plurality of slits therein, at least two of which are positioned in surfaces opposite to each other, said slits being substantially uniform in width throughout their length and originating at the open second end and terminating at a point in the sidewall;
   provided that when said shell corresponds to the configuration and dimension of a tooth selected from the group consisting of a pre-molar, a canine and an incisor, said surfaces opposite each other are the mesial and distal surfaces and when said shell corresponds in configuration and dimension to a molar tooth, said surfaces opposite to each other are the lingual and buccal surfaces, respectively.
   c. applying a dental cement filler to the inside surfaces of said shell;
   d. forcing said crown form onto the shaped tooth so that a portion of said filler is expressed through said means for fluid communication, to the exterior of said shell and into contact with adjacent teeth;
   e. allowing said dental cement filler to set, whereby said crown form is held engaged to said shaped tooth and is supported to the adjacent teeth.

10. The method of claim 9 wherein said resin is a polycarbonate.

11. The method of claim 9 wherein said shell has a means on the inner surface of the sidewall thereof for retaining fluid dental cement.

12. The method of claim 9 wherein said dental cement filler comprises a polymerizable mixture of acrylic monomers and sets in about 15 seconds.

* * * * *